United States Patent
Tome-Alcalde et al.

(10) Patent No.: US 10,322,169 B2
(45) Date of Patent: Jun. 18, 2019

(54) PROCESS FOR PREPARING A POWDER COMPRISING A HUMAN COAGULATION FACTOR PROTEIN AND A LACTIC ACID POLYMER

(71) Applicant: Evonik Roehm GmbH, Darmstadt (DE)

(72) Inventors: Juan Tome-Alcalde, Madrid (ES); Norbert Windhab, Hofheim (DE); Melanie Liefke, Ober-Ramstadt (DE); Anne Benedikt, Frankfurt (DE); Jessica Müller-Albers, Darmstadt (DE); Tom Tice, Indian Springs, AL (US); Susanne Ullrich, Darmstadt (DE); Andrea Engel, Frankfurt (DE); Matthias Germer, Langen (DE); Steffen Kistner, Frankfurt (DE); Jens Daufenbach, Mainz (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 15/735,161

(22) PCT Filed: Jun. 6, 2016

(86) PCT No.: PCT/EP2016/062775
§ 371 (c)(1),
(2) Date: Dec. 8, 2017

(87) PCT Pub. No.: WO2016/198351
PCT Pub. Date: Dec. 15, 2016

(65) Prior Publication Data
US 2018/0153967 A1    Jun. 7, 2018

Related U.S. Application Data

(60) Provisional application No. 62/173,726, filed on Jun. 10, 2015.

(51) Int. Cl.
| A61K 38/00 | (2006.01) |
| A61K 38/36 | (2006.01) |
| A61K 9/16 | (2006.01) |
| A61K 9/19 | (2006.01) |
| A61K 38/48 | (2006.01) |
| A61K 38/49 | (2006.01) |
| A61K 47/34 | (2017.01) |
| A61K 9/51 | (2006.01) |

(52) U.S. Cl.
CPC ............ *A61K 38/36* (2013.01); *A61K 9/1647* (2013.01); *A61K 9/19* (2013.01); *A61K 38/4846* (2013.01); *A61K 38/4866* (2013.01); *A61K 38/49* (2013.01); *A61K 9/5153* (2013.01); *A61K 47/34* (2013.01)

(58) Field of Classification Search
None
See application file for complete search history.

(56) References Cited

U.S. PATENT DOCUMENTS

| 5,610,266 A | 3/1997 | Buchholz |
| 6,113,948 A | 9/2000 | Heath et al. |
| 6,495,164 B1 | 12/2002 | Ramstack et al. |
| 6,706,854 B2 | 3/2004 | Buchholz et al. |
| 7,371,406 B2 | 5/2008 | Ramstack et al. |
| 2004/0253305 A1 | 12/2004 | Luner et al. |
| 2005/0220887 A1 | 10/2005 | Herbert et al. |
| 2007/0014848 A1 | 1/2007 | Buchholz et al. |
| 2009/0196932 A1 | 8/2009 | Luner et al. |
| 2010/0159017 A1 | 6/2010 | Gamon et al. |
| 2011/0142930 A1 | 6/2011 | Luner et al. |
| 2011/0144301 A1 | 6/2011 | Enderle et al. |
| 2012/0004323 A1 | 1/2012 | Markland et al. |
| 2012/0282298 A1 | 11/2012 | Bodick et al. |
| 2012/0288534 A1 | 11/2012 | Bodick et al. |
| 2014/0242170 A1 | 8/2014 | Bodick et al. |
| 2014/0356437 A1 | 12/2014 | Bodick et al. |
| 2015/0025050 A1 | 1/2015 | Bodick et al. |
| 2016/0015792 A1 | 1/2016 | Hendricus Van Pinxteren et al. |

FOREIGN PATENT DOCUMENTS

| EP | 0 427 185 | 5/1991 |
| EP | 0 805 678 | * 11/1997 |
| EP | 1 468 035 | 7/2005 |
| EP | 1 283 699 B1 | 6/2007 |
| EP | 2 201 940 A1 | 6/2010 |
| EP | 2 263 707 A | 12/2010 |
| EP | 1 907 023 B1 | 11/2011 |
| EP | 2 147 036 B1 | 3/2017 |
| WO | 1996/020698 A2 | 7/1996 |
| WO | 1997/044015 A1 | 11/1997 |
| WO | 2007/009919 A2 | 1/2007 |
| WO | 2014/135689 A2 | 9/2014 |

OTHER PUBLICATIONS

International Search Report and Written Opinion dated Sep. 12, 2016, in PCT/EP2016/062775, filed Jun. 6, 2016.

* cited by examiner

*Primary Examiner* — Jeanette M Lieb
(74) *Attorney, Agent, or Firm* — Grüneberg and Myers PLLC

(57) ABSTRACT

A process for preparing a powder, which includes one or more human coagulation factor proteins and a lactic acid polymer, involves mixing and dispersing a lactic acid polymer with a particle size $d_{50}$ in the range 0.1-2 μm and the one or more human coagulation factor proteins in water. The dispersion is dried, and the resulting dried mass is compressed. The resulting compressed dried mass is comminuted to a powder with a particle size $d_{50}$ in the range of more than 0.5 and up to 5 μm.

17 Claims, No Drawings

PROCESS FOR PREPARING A POWDER COMPRISING A HUMAN COAGULATION FACTOR PROTEIN AND A LACTIC ACID POLYMER

FIELD OF THE INVENTION

The invention is in the field of powders comprising a human coagulation factor protein and a lactic acid polymer.

TECHNICAL BACKGROUND

EP 1283699B1 describes injectable suspensions having improved injectability properties. The compositions disclosed are suitable for injection through a needle ranging in diameter from 18-22 gauge into a host. The compositions may disclose microparticles based on polylactic acids wherein an active agent is dispersed or dissolved. The mass median diameter of said microparticles may be in the range of 20-150 µm.

US2012/0004323A1 describes implant processing methods for thermally labile and other bioactive agents and implants prepared for the same. The process comprises admixing a composition comprising a bioresorbable polymer and a bioactive agent to form an admixture and processing the admixture into an implant at a temperature that is no greater than 70° C. In the examples poly(lactide-co-glycolide) polymer particles were grinded in a frozen state to a powder. Bovine serum albumin (BSA) was added as powder to the polymer powder and mixed using a glass mortar and pestle. The mixture was pressed in a tablet press to produce an implant. Mixing and pressing is performed preferably at or below room temperature. The implants had a minimum hardness (breaking pressure) of 25 lbs. In a release test the implants release the BSA to 100% in 2 days. Implants that were dip-coated in organic solvents like dichloromethane before released the BSA much slower, for instance to only 50% after 7 days.

The complex from factor VIII and von-Willebrand-factor (vWF) consists of the two molecules from factor VIII and von-Willebrand-factor (vWF) with different physiological functions. If factor VIII is injected it binds in the blood circulation to the von-Willebrand-factor (vWF) which activates factor VIII. The activated factor VIII effects as cofactor of the activated factor IX und accelerates the generation of activated factor X (factor Xa) out of factor X. Factor Xa activates prothrombin to thrombin which sets the fibrin free from the fibrinogen which starts the clotting procedure.

Haemoctin® is a commercially available human factor VIII preparation produced by Biotest AG, Dreieich, Germany, which originates from human blood serum. Public information is available on the web sites of the Paul-Ehrlich-Institut, Germany, and the German ministry of health (s. for instance http://www.pei.de/SharedDocs/arzneimittel/am-aus-blut/gerinnungsfaktor/16841-00-00.html). Haemoctin® is currently available in three concentrations Haemoctin® SDH 250, 500 and 1000 (referring to international Units (I.E.) of factor VIII). Beside factor VIII Haemoctin® contains glycine, sodium chloride, sodium citrate, calcium chloride and water as a carrier for injection. Haemoctin® is indicated for the treatment of haemophilia A (inherited factor VIII deficiency). The product contains the von-Willebrand-factor (vWF) in not physiological concentration and is therefore not indicated for the treatment of the von-Willebrand-disease.

OBJECT AND SOLUTION

It was an object to provide a process for preparing a human coagulation factor protein formulation using a lactic acid polymer. The powder should be suitable to be suspended in water for injection, preferably for intravenous injection, into a human being. The powder provided should be suitable for the treatment of blood clotting related deficiencies or diseases. The process should provide a powder that carries one or more human coagulation factor proteins in a nanostructured matrix and releases these proteins in a sustained manner. The process itself should be a soft process that preserves the therapeutic or cascading blood clotting activity of the coagulation factor protein without or with only little losses in activity.

The object was solved by

A process for preparing a powder comprising one or more human coagulation factor proteins and a lactic acid polymer, comprising the steps of a) mixing and dispersing the human coagulation factor protein and the lactic acid polymer with a particle size $d_{50}$ in the range 0.1-2 µm and the one or more human coagulation factor proteins in water, b) drying the dispersion, c) compressing the dried mass from the dispersion, d) comminuting of the compressed dried mass dispersion to a powder with a particle size $d_{50}$ in the range of more than 0.5 and up to 5 µm.

ADVANTAGEOUS EFFECTS

The process as disclosed herein provides a powder comprising one or more human coagulation factor proteins and a lactic acid polymer which can be suspended in water as a pharmaceutical composition suitable for injection preferably intravenous injection with an unexpected increased half-life time of the included human coagulation factor protein(s).

DETAILED DESCRIPTION

Particle Size Measurement

The determination of the particle size, especially the particle sizes in step a) and step d) as disclosed herein, may be performed according to the United States Pharmacopeia 36 (USP) chapter <429> and European Pharmacopeia 7.0 (EP) chapter 2.9.31. The particle size distribution is determined utilizing a laser scattering instrument (e.g. Fa, Sympatec GmbH, type HELOS equipped with RODOS dry dispersing unit). The laser diffraction method is based on the phenomenon that particles scatter light in all directions with an intensity pattern that is dependent on particle size. A representative sample, dispersed at an adequate concentration in a suitable liquid or gas, is passed through the beam of a monochromic light source usually from a laser. The light scattered by the particles at various angles is measured by a multi-element detector, and numerical values relating to the scattering pattern are then recorded for subsequent analysis. The numerical scattering values are then transformed, using an appropriate optical model and mathematical procedure, to yield the proportion of total volume to a discrete number of size classes forming a volumetric particle size distribution (e.g. $d_{50}$ or $d_{(0.5)}$ describes a particle diameter corresponding to 50% of cumulative undersize distribution; $d_{90}$ or $d_{(0.9)}$ describes a particle diameter corresponding to 90% of cumulative undersize distribution). Preferably the determination of particle size distribution may be carried out by a Beckman Coulter@® LS.

DEFINITIONS

The term "room temperature" in the sense of the invention may be 20-25° C., about 22° C. or 22° C.

The term "water" preferably means demineralized water or pure water. The use of "water" in the form of aqueous solutions, such as physiological saline or phosphate buffered saline (PBS) may be possible but is less preferred, due to the risk of possible ionic side effects.

Process

The process for preparing a powder comprising one or more human coagulation factor proteins and a lactic acid polymer comprises the steps a) to d). The application of organic solvents which could inactivate or reduce the biological activity of the one or more human coagulation factor proteins is avoided. The process is therefore preferably free from any addition of organic solvents in concentrations which can inactivate or reduce the biological activity of the one or more human coagulation factor proteins or free from organic solvents at all.

Step a)

In step a) the lactic acid polymer with a particle size $d_{50}$ in the range 0.1-2, 0.2-1.5, 0.3-1.2, 0.6-1.0 µm and the human coagulation factor protein are mixed and dispersed in water.

Preferably the human coagulation factor protein is comprised in a human blood plasma preparation. Preferably the ratio between the human blood plasma preparation, which comprises the human coagulation factor protein, and the lactic acid polymer is from 30:70 to 1:99, 20:80 to 2:98, 15-85 to 5:95 parts by weight. The optimum for factor VIII comprised in a human blood plasma preparation (in the form of Haemoctin®) and poly(lactide-co-glycolide), lactide/glycolide ratio 50:50, was about 10:90 parts per weight. At or around this ratio the optimum homogeneity of the mixture in step b) (measured by EDX analysis) and the optimum of the half-life time of the powder from step d) (measured by BIOPHEN® chromogenic assay for factor VIII) was found (s. the examples).

Step b)

In step b) the dispersion from step a) is dried to give a dried mass. The drying step may be carried out by spray drying, preferably at temperatures of not more than 45, not more than 40, not more than 30° C. or from 20 to 30° C. Most preferred the drying step may be carried out by lyophilisation. The resulting intermediate product may have the form of an irregular powder. EDX analysis of this step show an advantageous homogeneous distribution when the human coagulation factor protein and the lactic acid polymer are mixed with each other and dispersed in water and are then dried by lyophilisation.

Step c)

In step c) the dried mass obtained from the dispersion from step b) is compressed. Compression is preferably carried out in a tablet press with comparably low pressures to avoid or to reduce a possible inactivation of the one or more human coagulation factor proteins. The compression of dried mass from the dispersion may be performed at a compression force from 0.1 to 2 or 0.2 to 1.8, 0.3 to 1.0, 0.4 to 0.6 kN (cross section area of 78.54 mm²). It is assumed that this compressing step is essential for creating a three dimensional lactic acid polymer structure with a high inner surface to which the human coagulation factor protein is attached at high loading level. A key factor therefore seems to be the use of the lactic acid polymer with a nano scale particle size as defined in step a).

The assumed interaction caused by the compression step of the components, human coagulation factor protein and lactic acid polymer becomes apparent by analysis via attenuated total reflectance infrared spectroscopy (ATR-IR) in the wave-length range of the amide I band, wave-number area 1500.000-1700.000 $[cm^{-1}]$. The single components, human coagulation factor protein and lactic acid polymer alone, in comparison to the compressed components show clearly different absorption spectra (s. examples).

Step d)

In step d) the compressed dried dispersion is comminuted to a powder with a particle size $d_{50}$ in the range of more than 0.5 and up to 5, 0.6 to 3, 0.8 to 2, 0.9 to 1.5 µm. Preferably the particles may be of regular, spherical shape. The rather low particle size allows the powder to be suspended in water, where it becomes suitable or readily available for parenteral application, preferably for the intravenous injection of the particles.

Human Coagulation Factor Proteins

The one or more human coagulation factor proteins may be selected from factor I=fibrinogen, factor II=prothrombin, factor III=tissue factor, factor V=proaccelerin, factor VII=proconvertin, factor VIII=antihemophilic factor A, factor IX=antihemophilic factor B, factor X=Stuart Prower factor, factor XI=plasma thromboplastin antecedent, factor XII=Hageman factor, factor XIII=fibrin-stabilizing factor, von Willebrand factor, prekallikrein, antithrombin III, heparin cofactor II, Protein C, Protein S, protein Z, protein Z-related proteinase inhibitor, plasminogen, alpha-plasma 2-antoplasmin, tissue plasminogen activator, urokinase, plasminogen activator inhibitor-1 and plasminogen activator inhibitor-2 or any combinations thereof.

The human coagulation factor protein may be of natural origin, isolated from human blood plasma, or may be a recombinant human coagulation factor protein, manufactured by recombinant DNA techniques.

An example for a human coagulation factor protein of natural origin isolated from human blood plasma is the commercially available product Haemoctin® respectively Haemoctin® SDH 250, 500 and 1000 (the number is referring to international Units (IU) of factor VIII) manufactured by the Biotest AG, Germany. Similar products from other manufacturers may be commercially available as well.

An example for a recombinant human coagulation factor protein is the commercially available product Advate® respectively Advate® 250 (distributed by Baxter Deutschland GmbH, Germany).

Preferably the human coagulation factor protein may be comprised in a human blood plasma preparation.

Preferably the human coagulation factor protein, comprised in a human blood plasma preparation, may be factor VIII (FVIII), factor IX or the von Willebrand factor (vWF) or any combination thereof. Preferably the ratio of vWF/FVIII in the human blood plasma preparation may be 0.1 to 0.5, 0.2 to 0.4 International Units (IU) vWF per 1 IU FVIII.

Preferably the human blood plasma preparation may comprise the von Willebrand factor in a not-physiological concentration. A not-physiological concentration may be a concentration that is not indicated for the treatment of the von-Willebrand-disease. A not-physiological concentration in International Units (IU) may be at least 2-, 3-, 10-, 20-, 50- or 100-times below the normal or average concentration or out of the range of the normal or average concentration of the von Willebrand factor in the blood plasma of a healthy human being.

Preferably the human blood plasma preparation comprises 0.05 to 5% by weight of human factor VII and 95 to 99.95% by weight of other plasma proteins or further pharmaceutical excipients or both. Such a concentration may be defined as a physiological or therapeutically efficient concentration.

A suitable human blood plasma preparation which comprises the von Willebrand factor in a not-physiological concentration and human factor VIII in a physiological or therapeutically efficient concentration (0.3 U VWF/1 U FVIII) may be the commercially available product Haemoctin® SDH 250, 500 and 1000 (the number is referring to international Units (IU) of factor VIII) manufactured by the Biotest AG, Germany.

Preferably a suitable the human blood plasma preparation may comprise 25 to 1000, 100 to 800, 100 to 300, 150 to 250 IU/mL of human factor VIII protein activity at a concentration of 100 mg/mL water.

The human coagulation factor protein may be a recombinant protein manufactured by recombinant DNA techniques, such as recombinant factor VIII. A suitable recombinant Factor VIII preparation may be in the range of 500 to 1000, 600 to 900 or 700 to 800 IU/ml of human Factor VIII protein activity at a concentration of 100 mg/mL water.

The Lactic Acid Polymer.

The term "lactic acid polymer" (polylactic acid) shall mean polymers or copolymers comprising polymerized monomer units, preferably at least 10, at least 20, at least 30, at least 40, at least 50, at least 60, at least 70% by weight or up to 100% of polymerized lactic acid or lactide units. The lactic acid polymer may have a particle size $d_{50}$ in the range of 0.1-2, 0.2-0.15, 0.5-1.2, 0.6-1.0 µm.

Lactic acid polymer products with particle sizes in the required range are commercially available.

Lactic acid polymer products which are not in distinct powder form or which consist of powder particles with higher $d_{50}$ values as required may be adapted by a skilled person to a suitable particle size by common methods such as milling or high pressure homogenization. High pressure homogenization is preferably performed by employing high pressure homogenization equipment. The lactic acid polymer may be dissolved in a small volume of organic solvent such as methylene chloride or ethyacetate to form a polymer solution. An excess of water may then be added to the polymer solution to form an emulsion which may be homogenized under pressure. The organic solvent may then be removed from the emulsion by vacuum to gain a fine polymer particle dispersion. Lactic acid polymer particles within the required range may be subsequently gained from polymer particle dispersion by removing the water in a drying step.

A lactide is a cyclic di-ester of lactic acid. The term lactide shall mean L-lactide, D-lactide, D,L-lactide or meso-lactide. Suitable comonomers that may be polymerized with the lactic acid or lactide respectively are glycolide, epsilon-caprolactone, trimethylene carbonate or dioxanone. Lactic acid polymers or copolymers may include also an AB- or ABA-blockcopolymer containing an A-block selected from lactic acid polymers or copolymers and a B-block selected from a polyethylenglycol polymer.

The one or more lactic acid polymers may preferably be selected from lactic acid polymers or copolymers synthesized from monomer components or from a mixture of monomer components selected from the group consisting of a) to l):

a) D- and L-lactide,
b) L-lactide and glycolide,
c) D,L-lactide and glycolide,
d) L-lactide and epsilon-caprolactone,
e) L-lactide and dioxanone,
f) L-lactide and trimethylene carbonate,
g) L-lactide, D-lactide, meso-lactide or D,L-lactide,
h) L-lactide,
i) DL-lactide,
j) statistically distributed monomer units of L-lactide, D-lactide, meso-lactide or DL-lactide and epsilon caprolactone,
k) statistically distributed monomer units of L-lactide, D-lactide, meso-lactide or DL-lactide and dioxanone,
l) statistically distributed monomer units of L-lactide, D-lactide, meso-lactide or DL-lactide and trimethylene carbonate.

These kind of "lactic acid polymers" are biodegradable polymers and well known in the art for example from EP1468035, U.S. Pat. No. 6,706,854, WO2007/009919A2, EP1907023A, EP2263707A, EP2147036, EP0427185 or U.S. Pat. No. 5,610,266.

Preferably the lactic acid polymer is a copolymer polymerized from lactide and glycolide units (lactide-glycolide copolymer=PLGA).

Preferably the bio-resorbable polyester is a poly(D,L-lactide-co-glycolide) copolymer preferably with an inherent viscosity (IV) from 0.1 to 2.0, 0.12 to 1.2, 0.14 to 1.0, 0.16 to 0.44, 0.16 to 0.24 [dL/g].

A preferred bio-resorbable polyester is a poly(D,L-lactide-co-glycolide) copolymer with a proportion of polymerized D,L-lactide:glycolide units in the poly(D,L-lactide-co-glycolide) copolymer from 80:20 to 20:80, 70:30 to 30:70, 60:40 to 40:60 or 80:20 to 60:40 parts by weight or per mole (molar ratio), whereby the amounts of D,L-lactide:glycolide add up to about 100%.

A preferred bio-resorbable polyester is of the type of RESOMER® RG 503 or RESOMER® RG 503 H which are a poly(D,L-lactide-co-glycolide)-copolymers with a D,L-lactide:glycolide ratio of 45:55 to 55:45 (molar ratio), preferred 50:50, and with an inherent viscosity IV in the range of 0.28 to 0.48 or 0.3 to 0.46 [dL/g].

A preferred bio-resorbable polyester is of the type of RESOMER® RG 502 or RESOMER® RG 502 H which are a poly(D,L-lactide-co-glycolide)-copolymers with a D,L-lactide:glycolide ratio of 45:55 to 55:45 (molar ratio), preferred 50:50, and with an inherent viscosity IV in the range of 0.16 to 0.44 or 0.16 to 0.24 [dL/g].

The bio-resorbable polyester may be characterized by a glass transition temperature $T_g$ from about 30 to 60, 35 to 55° C. The glass transition temperature may be preferably determined according to the United States Pharmacopeia 36 (USP) chapter <891>, European Pharmacopeia 7.0 (EP) chapter 2.2.34 and according to DIN 53765:1994-03 (D).

The term "bio-resorbable" in "bio-resorbable polyester" means that the polyester, which is preferably a lactid acid based polymer, is after implantation or injection in the human body or in the body of an animal in contact with the body fluids broken down into oligomers in a slow hydrolytic reaction. Hydrolysis end products such as lactic acid or glycolic acid are metabolized into carbon dioxide and water. Other exchangeable expressions for the term "bio-resorbable polyester" which are often used are "resorbable polyester", "bio-degradable polyester" or "adsorptive polyester".

Powder

The application includes a powder obtainable or obtained from a process as disclosed with a particle size $d_{50}$ in the range of more than 0.5 and up to 5 µm, 0.6 to 3, 0.8 to 2, 0.9 to 1.5 µm comprising a human coagulation factor protein and a lactic acid polymer.

Pharmaceutical Composition

The application also discloses a pharmaceutical composition comprising the powder as disclosed in dry, dispersed or dissolved form. The pharmaceutical composition may further comprise water as carrier liquid for the dispersed or dissolved form and/or pharmaceutical acceptable excipients, such as salts, buffers or stabilizers. The application includes the use of the powder for producing a pharmaceutical composition suitable for the treatment of a disease or a genetic disorder associated with the human coagulation factor protein.

EXAMPLES

Materials:

TABLE 1

Chemical compounds used for preparation of binary mixtures

| Material | Supplier |
|---|---|
| PLGA (RESOMER ® RG 503 H) | Evonik Industries AG (Darmstadt, Germany) |
| Haemoctin ® SDH 250/500/1000 | Biotest AG (Dreieich, Germany) |
| TRIS 99%, Ph. Eur. | Carl Roth GmbH & Co. KG (Karlsruhe, Germany) |
| Sodium chloride, p. A. | Merck KGaA (Darmstadt, Germany) |
| Hydrochloric acid, 1N (Titrisol) | Merck KGaA (Darmstadt, Germany) |
| Ethyl acetate | Avantor Performance Materials Deutschland (Grießheim, Germany) |
| Water for cell culture | Merck Millipore (Darmstadt, Germany) |
| Advate ® 250 | Baxter Deutschland GmbH (Unterschleißheim, Germany) |

TABLE 2

Chemical compounds for production of milled samples

| Material | Supplier |
|---|---|
| PLGA particle preparation LSB 5050 DLG 2A (LAKESHORE BIOMATERIALS ™), the particle size was $d_{50}$ = 741 nm | Evonik Degussa Corporation (Birmingham, United States) |
| Haemoctin ® SDH 1000 | Biotest AG (Dreieich, Germany) |
| FIX = factor IX (1000 IU) | Biotest AG (Dreieich, Germany) |
| vWF = von Willebrand factor (1000 IU) | Biotest AG (Dreieich, Germany) |
| Water for cell culture | Merck Millipore (Darmstadt, Germany) |

TABLE 3

Chemical compounds for sample characterization

| Material | Supplier |
|---|---|
| HYDRANAL ® Titrant 2 with HYDRANAL ® Solvent | Sigma-Aldrich Chemie GmbH (Taufkirchen, Germany) |
| Formamide | Sigma-Aldrich Chemie GmbH (Taufkirchen, Germany) |
| Water for cell culture | Merck Millipore (Darmstadt, Germany) |
| Chromogenic assay Factor VIII:C; BIOPHEN ® | CoaChrom Diagnostica GmbH (Maria Enzersdorf, Austria) |
| Factor VIII Deficient Plasma, CryoCheck ® | CoaChrom Diagnostica GmbH (Maria Enzersdorf, Austria) |
| Human Coagulation Factor VIII Concentrate BRP | EDQM Council of Europe (Strasbourg, France) |
| Acetic acid | Merck KGaA (Darmstadt, Germany) |
| Bradford solution for protein determination | AppliChem GmbH (Darmstadt, Germany) |

TABLE 4

Devices used for production process

| Device | Provider |
|---|---|
| Single punch eccentric tablet press ERWEKA EP-1, tool set for 10 mm round biconvex tablets | Erweka GmbH (Heusenstamm, Germany) |
| Safety cabinet HERA Safe 2020 | Thermo Fisher Scientific GmbH (Dreieich, Germany) |
| Vario-Planetary mill PULVERISETTE 4 | Fritsch GmbH (Idar-Oberstein, Germany) |
| Analytical balance Sartorius ME215S-OCE | Sartorius AG (Gottingen, Germany) |
| Freeze dryer EPSILON 2-6 D | Martin Christ GmbH (Osterode am Harz, Germany) |
| Qwik Handi-Press with 7 mm die set | Thermo Spectra-Tech Inc. (Shelton, United States) |

TABLE 5

Devices used for analytical characterization (biological/physicochemical)

| Device | Provider |
|---|---|
| Laser Diffraction Particle Size Analyzer, Beckman Coulter LS | Beckman Coulter GmbH (Krefeld, Germany) |
| Karl Fischer compact titrator | Mettler-Toledo GmbH (Gießen, Germany) |
| Scanning electron microscope JEOL JSM-840A-Point with EDX unit INCA 200 | point electronic GmbH (Halle, Germany) |
| Sputter Polaron | Bio-Rad Laboratories GmbH (Munchen, Germany) |
| Rotary microtome | Leica Mikrosysteme Vertrieb GmbH (Wetzlar, Germany) |
| Multiplate-reader TECAN Infinite 200 Pro | Tecan Group Ltd. (Männedorf, Switzerland) |
| Micro pipette 2-20 µL, 20-100 µL, 100-1000 µL | Eppendorf AG (Hamburg, Germany) |
| Heating thermo shaker HTMR 133 | DITABIS Digital Biomedical Imaging Systems AG (Pforzheim, Germany) |
| 96 Well Polystyrene cell culture microplates, clear | Greiner Bio-One GmbH (Frickenhausen, Germany) |
| Universal oven UNB 200 | Memmert GmbH + Co. KG (Schwabach, Germany) |
| Nicolet FT-IR spectrometer with additionally ATR unit (smart orbit) | Thermo Electron Corporation (Langenselbold, Germany) |

Methods:

Binary Mixtures for Activity Determinations and Kinetics

As general rule, mother solutions or dispersions of the different formulation constituents were prepared and mixed at adequate amounts (in a 1:1 v/v mixture) to achieve reference (Haemoctin® with e.g. 100 IU activity), placebo (PLGA supernatant (RESOMER® 503 H) of a 10 mg/1.5 mL dispersion), ethylacetate (watersoluble fraction) and different working mixtures (e.g. mixtures of two components called binary mixtures) in phosphate buffered saline (PBS) pH 7.4 [Monograph '4.01.03 Buffer solutions' of PhEur], with activity levels within the determination range of the activity test. Usually, an activity about 1 IU/mL (IU=international units) was the intended aim, as this is per definition, the desired activity level of FVIII in healthy humans. All sample preparations were conducted under aseptic conditions to avoid contamination.

Activity Assay Binary Mixtures

The determination of the Blood factor VIII activity was carried out with the commercially available BIOPHEN® chromogenic assay kit Factor VIII:C from CoaChrom Diagnostica (assay principle in short: When activated by thrombin, Factor VIII:C forms an enzymatic complex with Factor IXa, phospholipids and calcium, which activates Factor X to Factor Xa. Factor Xa cleaves the substrate and releases pNA/para-Nitroanilin. The amount of pNA generated is directly proportional to the Factor Xa activity.). Binary mixtures of Haemoctin® with components of possible formulation approaches as well as possible solvents to be used for formulation approaches were tested as samples for the activity assays. All the samples were prepared with a final expected protein concentration of about 1 mg/mL and an expected activity of about 100 IU/mL.

As a preparation step for the activity assay each of the kit reagents R1-3 are reconstituted in 2.5 mL cell culture water, then mixed by vortexing and incubated for 30 min at room temperature (18-25° C.). Afterwards the reagents have to be pre-incubated at 37° C. for the test.

As next step calibration plasma was prepared for the activity standard line. Therefore lyophilized plasma was reconstituted in 1 mL cell culture water, then mixed by vortexing and as well incubated for 30 min at room temperature. The calibration plasma contained now an activity of around 70%. This calibration plasma should be used for a calibration line starting with 200% activity and including an internal assay dilution of 1:40. Therefore the plasma was diluted 1:14 (100 µL calibrator plasma added to 1300 µL Tris-BSA buffer (R4+); based on the equation 200×concentration of the plasma/100), while all the samples were diluted 1:40. Thus starting with 200% activity the following calibration line is prepared:

TABLE 6

Dilution steps for the BIOPHEN ® calibration line of Blood factor VIII activity

| % FVIII:C | 200% solution VIII:C calibrator plasma [µL] | Tris-BSA buffer (R4+) [µL] |
|---|---|---|
| 200 | 500 | 0 |
| 100 | 250 | 250 |
| 50 | 125 | 375 |
| 25 | 62.5 | 437.5 |
| 1.25 | 62.5 | 875 |
| 6.25 | 62.5 | 1750 |
| 0 | 0 | 500 |

50 µL/well of each concentration were applied in triplicates to a 96 well plate; additional three wells of 50 µL Tris-BSA buffer R4+ were used as background reference.

Referring to the preparation of the test samples, all of them were diluted to a concentration of 0.2-2 IU/mL prior to the assay performance. Thus the Haemoctin® samples were primarily diluted 1:100 (expected activity of 1 IU/mL) in Tris-BSA buffer. Furthermore every sample was diluted additionally 1:40 due to the internal assay dilution (see calibration line with plasma calibrator). Again triplicates of 50 µL per well were added to the 96 well-plate.

After applying all samples, controls and the calibration line to the 96 well plate, the following assay steps were performed:
- addition of 50 µL R1 (kit reagent 1, Human Factor X and fibrin polymerization inhibitor, pre-incubated at 37° C.)
- addition of 50 µL R2 (kit reagent 2, Factor IXa, with thrombin, phospholipids and calcium, pre-incubated at 37° C.) 5 min incubation at 37° C.
- addition of 50 µL R3 (kit reagent 3, Factor Xa specific chromogenic substrate, pre-incubated at 37° C.) exactly 5 min incubation at 37° C. addition of 50 µL of acetic acid, 20%

The measurement of absorptions should be carried out within 2 h at 405 nm by the means of a multiplate-reader.

For data analysis the absorption of Tris-BSA buffer (R4+) was subtracted from all the samples, including the calibration series, and the mean values were calculated. After preparation of the calibration line, the FVIII:C activities of the samples could be calculated using the equation of the calibration line.

To obtain the final results the dilution steps prior to the assay (1:100 and 1:40) had to be taken into account by using the following calculation:

Activity [%]*100/40

The resulting values display the activity of the samples.
Lyophilisation of Blood Factor/PLGA Formulation and Haemoctin® Control ~450 mg of pre-loosened blood factor product (e.g. Haemoctin®) are transferred into a glass beaker, that had to be cleaned with 2-propanol, before adding ~4.09 g of PLGA (LSB 5050 DLG 2A, d50=741 nm). After addition of ~70 mL water for cell culture and gentle manual swiveling, the obtained suspension had to be filled quantitatively (max. 5 mL, max. liquid height to ensure proper lyophilisation process) into 30 mL beaded bottles, followed by a lyophilisation process.

As control, one vial of Haemoctin® SDH 1000 was dissolved in 5 mL of water for cell culture and lyophilised with the same procedure as the Haemoctin®/PLGA (LSB 5050 DLG 2A, d50=741 nm) formulation.

TABLE 7

Device settings for lyophilisation process

| Process phase | Time (hh:mm) | Temperature (° C.) | Vacuum (mbar) |
|---|---|---|---|
| Loading | 00:00 | +20 | — |
| Freezing | 02:00 | −30 | — |
| Freezing | 02:00 | −30 | — |
| Freezing | 01:00 | −20 | — |
| Freezing | 00:30 | −20 | — |
| Primary Drying | 00:01 | −20 | 0.85 |
| Primary Drying | 01:59 | −20 | 0.85 |
| Primary Drying | 01:00 | −10 | 0.85 |
| Primary Drying | 01:00 | −10 | 0.85 |
| Primary Drying | 01:00 | 0 | 0.85 |
| Primary Drying | 10:00 | +10 | 0.85 |
| Secondary Drying | 00:01 | +10 | 0.001 |
| Secondary Drying | 00:59 | +10 | 0.001 |

Final storage of the prepared lyophilised formulation should be in the same 30 mL glass bottles, closed with a butyl rubber stopper and aluminium cap seal, at +2° C. to +8° C.

Energy Dispersive X-Ray Spectroscopy (EDX) Analysis Haemoctin® Formulation)

The EDX measurement was carried out using a scanning electron microscope including the specific EDX unit.

The tablets derived from Handi-Press were fixed directly on an aluminium sample plate containing a self-adhesive graphite pad and steamed for a defined time with a thin carbon layer. The surface was measured afterwards, while for cut surface the tablet was cut using microtome to avoid artifacts or shadowing effects during the EDX analysis.

Tableting of Lyophilised Blood Factor Product/PLGA Formulation

Before tableting, all device parts of the single punch tablet press, which get in contact with the ingredients, had to be cleaned with 2-propanol, to avoid microbiological contamination of the final tablets. Afterwards ~200 mg of the formulation 90% as lyophilisate should be filled in by hand (using spatula) into the lower punch at the feeding position (lowest position in the cycle) and compressed to tablets.

The advance/compression depth setting of the upper punch was adjusted to about 1.25 to produce low pressed tablets; setting of the upper punch was adjusted to about 2.00 to produce strong pressed tablets. Applied pressures for tablet compression were in the range of 0.4-0.6 kN.

Milling of Improved Lyophilised Formulation 90%

The grinding bowls and grinding balls were thoroughly cleaned and autoclaved before milling process to avoid microbiological contamination of the final milled product; the filling step of test material into the bowl as well as the sampling (final milled product/analytical sample) should also be carried out under aseptic conditions.

A minimum of approximately 2 g of prepared blood factor/PLGA (LSB 5050 DLG 2A, d50=741 nm) tablets were loaded into the sterile grinding bowls and packaged into PE bags for safety aspects. Once closed, the grinding bowls could be transferred outside the sterile workbench. After assembling the 'ready-to-use' grinding bowls into the device, the milling process could be carried out as described in Table 8.

TABLE 8

Process parameters for milling processes (strong and soft)

| Parameter | Setting for milling condition 1 (strong) | Setting for milling condition 2 (soft) |
|---|---|---|
| Grinding bowl | 45 mL volume | 45 mL volume |
| Grinding balls | 190 pieces per bowl; 5 mm; zirconium oxide | 190 pieces per bowl; 5 mm; zirconium oxide |
| Cycle | 1 × 1 min | 1 × 1 min |
| Relative ratio of supporting disks | 1:−2 | 1:−1 |

Finally, the water content of the obtained milled formulation should be ≤3%, as determined by Karl-Fischer titration.

Determination of Particle Size Distribution

The determination of particle size distribution was carried out by Beckman Coulter® LS. Table 9 gives an overview about the device settings which were used for the sample measurement.

TABLE 9

Device settings of Beckman Coulter LS 13 320

| Parameter | Setting |
|---|---|
| Particle Size Analysis Range | 0.4 µm to 2000 µm |
| Sample Module | Micro Liquid Module (MLM) |
| Diffraction Illuminating Source | Solid State (780 nm) |
| Humidity | 0% to 90%, non-condensing |
| Temperature Range | 10° C. to 40° C. |
| Typical Analysis Time | 15 s to 90 s |

TRIS buffer pH 7.9, water for cell culture and/or Tween® 20 (10% w/w) were used during the project as background references and suspension media. The sample (a spatula point) has to be suspended in the preferred suspension media before measurement. If needed, partially short ultrasonic treatment of the samples was carried out, beside swiveling and inverting.

Activity Assay Kinetics of Tablets and Milled Samples

The determination of the blood factor VIII activity as tablet or milling sample was performed with the commercially available BIOPHEN® Chromogenic assay kit Factor VIII:C from CoaChrom Diagnostica. Unmilled tablets were made of Haemoctin® with different amounts of polymer as well as recombinant FVIII (Advate®) and with or without vWF, while milled samples contained polymer and Haemoctin®, only. Every tablet or milled sample was produced in triplicates and used as samples for the activity assays.

For the assay performance, tablets were cut into pieces using a cleaned pill splitter and weighed to a final expected protein activity of 1 IU/mL, respectively. Every piece of tablet was filled up with 1 mL or 2 mL deficient plasma and incubated up to 7 days (7d) in the heating thermo shaker at 37° C. with 600 rpm.

All working steps were done under aseptic conditions to avoid contamination of plasma during incubation. Deficient plasma was filtered (0.2 µm pore size) before usage.

For each assay performance, a fresh vial of Haemoctin® was used.

For the calibration curve the standard Human Coagulation factor VIII Concentrate BRP from EDQM was used. Therefore lyophilised BRP Concentrate was reconstituted in 1 mL cell culture water to get a concentration of 10.4 IU/mL.

TABLE 10

Dilution steps for the EDQM calibration line for blood factor VIII activity

| Activity [IU/mL] | BRP Concentrate | Deficient Plasma [µL] |
|---|---|---|
| 1 | 15 µL correspond to 10.4 IU/mL | 141 |
| 0.5 | 50 µL correspond to 1 IU/mL | 50 |
| 0.25 | 50 µL correspond to 0.5 IU/mL | 50 |
| 0.125 | 50 µL correspond to 0.25 IU/mL | 50 |
| 0.0625 | 50 µL correspond to 0.125 IU/mL | 50 |
| 0.03125 | 50 µL correspond to 0.0625 IU/mL | 50 |

Due to the starting activity of the activity assay kinetic, internal assay dilutions of test samples and controls were optional required to adhere to the detection range of the BIOPHEN® Chromogenic assay kit factor VIII:C.

To include the internal assay dilution of 1:40, every test sample, control and sample of the calibration line was further diluted, meaning 5 µL sample added to 195 µL Tris-BSA buffer (R4+); thus 5 µL deficient plasma in 195 µL Tris-BSA buffer (R4+) served as background reference.

The activity assay was carried out as described under point "Activity assay binary mixtures".

ATR-IR spectroscopy (Attenuated Total Reflectance Infrared Spectroscopy)

A small amount of dry sample was pressed on a carrier crystal (diamond) at a defined ohmic resistance (200Ω), followed by measurement of a full spectrum at 4000 to 400 $cm^{-1}$ using a Nicolet FT-IR spectrometer with additional ATR unit. Afterwards for interpretation of interactions between used substances and/or process steps, the specific band amide I (1700-1500 $cm^{-1}$) was considered in detail meaning six interval areas with a wavenumber range of 33.333 $cm^{-1}$ were fixed as analysis points.

PLGA (LSB 5050 DLG 2A, d50=741 nm) alone shows almost no signal in the specific band amide I (1700-1500 $cm^{-1}$). The background noise however was subtracted from the formulation 90 spectrum.

Haemoctin® alone, factor IX (FIX) alone and von Willebrandt factor (vWF) alone show a significant signal in the specific band amide I (1700-1500 $cm^{-1}$), which was used as reference spectrum to be compared with that from the corresponding formulations (all formulations 90/10).

The formulation 90 (PLGA (LSB 5050 DLG 2A, d50=741 nm)+Haemoctin®, 90/10), formulation for factor IX (FIX) and formulation for von Willebrandt factor (vWF) show a significant signal in the specific band amide I (1700-1500 cm$^{-1}$), which is different from Haemoctin® alone.

The resulting sample values in the tables 16-18 display the percentage of each interval area to total (100%) measured amide I peak area.

Results:

Activity Assay and Kinetics

To analyse the compatibility of Haemoctin® with possible components of possible formulation approaches, binary mixtures of Haemoctin®, RESOMER® (aqueous phase of a suspension), ethyl acetate (aqueous phase of an emulsion) were tested in activity assays.

Table 11 shows that the changes in the assay procedure led to an activity of the normal plasma in the range of 80% activity as expected, confirming the absence of distinct mistakes in the assay procedure. In general the results showed that none of the formulation components (e.g. RESOMER® 503 H aqueous supernatant) tested caused any significant background signal in the activity assay. Beside that results of the mixture of Haemoctin® with these components indicate a tendency to higher activities compared to Haemoctin® alone (e.g. RESOMER® 503 H+Haemoctin®). Furthermore the presence of ethyl acetate led to a significant reduction of the activity to almost zero.

TABLE 11

Activity of binary mixtures (1:1) with possible formulation components and single components as controls.

| Samples (n = 3) | Activity (%) |
|---|---|
| Haemoctin® alone | 156.9 |
| normal plasma | 84.2 |
| Haemoctin® + Ethylacetate (aqueous phase) | 3.4 |
| Haemoctin® + Ethylacetate (evaporated) | 2.6 |
| RESOMER® 503 H (aqueous supernatant) | 0.2 |
| RESOMER® 503 H (aqueous supernatant) + Haemoctin® | 195.8 |

Following the first compatibility trials, different Haemoctin®/polymer ratios were used to prepare tablets. These tablets were tested for their FVIII activity in order to find the optimum ratio of Haemoctin® mixed and formulated with polymer. The optimum ratio should allow a prolonged half-life of FVIII activity by sustained release of Haemoctin® while ensuring at the same time a release that is fast enough to affect the activity in a time period of 7 days.

Table 12 displays that polymer ratios of 70-98% polymer influence the Haemoctin® activity as required, with an optimum at 90% polymer content.

TABLE 12

Activity kinetics of tablets with different Haemoctin®/polymer ratios

| Formulation description (n = 3) | Ratio Haemoctin® (%) | Ratio PLGA (%) | Tabletting (handmade with Handi-Press) | Percentage of remaining ~1 h | 2 d | 7 d |
|---|---|---|---|---|---|---|
| Haemoctin® (solution) | 100 | | | 100 | 83 | 56 |
| Formulation 30/Haemoctin® | 70 | 30 | X | 100 | 81 | 30 |
| Formulation 50/Haemoctin® | 50 | 50 | X | 100 | 80 | 34 |
| Formulation 70/Haemoctin® | 30 | 70 | X | 100 | 123 | 73 |
| Formulation 90/Haemoctin® | 10 | 90 | X | 100 | 200 | 129 |
| Formulation 94/Haemoctin® | 6 | 94 | X | 100 | 168 | 116 |
| Formulation 98/Haemoctin® | 2 | 98 | X | 100 | 154 | 115 |

To further optimize the formulation and to prepare a particle formulation suitable for intravenous administration (particle diameter ≤1 μm), the formulation 90% was used to perform the following process steps and is further mentioned as "formulation 90":

Step a): A suspension of the 90/10 mixture of polymer and Haemoctin® was prepared in water in order to achieve a homogenous mixture which ensures reduced deviations between different batches of the formulation.

Step b): The suspension was further lyophilised to remove the water again, which would interfere with the FVIII activity.

Step c): The lyophilised powder was compressed to allow the Haemoctin® components to adhere to the polymer.

Step d): As a final step of the process the tablets are milled down to a particle size about 1 μm to be suitable for intravenous administration and to allow further adhesion of Haemoctin® to the polymer.

The homogeneity mentioned under process step 1 was analysed via EDX (Energy dispersive X-ray spectroscopy). As the result of the EDX analysis, the following ions and their distribution in the samples are represented in a specific colour:

Red: Oxygen
Black/grey: Carbon
Green: Sodium
Blue: Chloride

Beside a low percentage of the FVIII protein present in Haemoctin® in general, the remaining ingredients in Haemoctin® are a mixture of amino acids, salts and stabilizers. Therefore the main focus was on the detection of sodium (green) and chloride (blue), which could be observed in the Haemoctin® EDX results and are not available in pure PLGA (LSB 5050 DLG 2A, d50=741 nm).

In several approaches to achieve homogeneity of the formulation mixture, the best homogeneity of a prepared PLGA (LSB 5050 DLG 2A, d50=741 nm) (90%)/Haemoctin® (10%) formulation was detectable after the lyophilisation process of the formulation suspension in water. Haemoctin® (green & blue) is uniformly distributed in the EDX test sample.

A good homogeneity based on the formulation manufacturing process by mixing PLGA with sieved Haemoctin® was not possible to achieve. The brighter spots of Haemoctin® were observed in the background of the red signal of PLGA (LSB 5050 DLG 2A, d50=741 nm).

Furthermore the measurement of the particle size and distribution was carried out; showing the best particle size distribution ($d_{50}$ of about 1 μm) for the milled mixtures of the improved formulation (PLGA (LSB 5050 DLG 2A, d50=741 nm) (90%)/Haemoctin® (10%)) tablets (low pressed, milling condition 2).

The particle size distribution of the milled formulation (PLGA (LSB 5050 DLG 2A, d50=741 nm) (90%)/Haemoctin® (10%), low pressed tablet, milling condition 2) after ultrasonic treatment (1 min) in 10% Tween® 20 was $d_{10}$: 0.574 μm/$d_{50}$: 1.252 μm/$d_{90}$: 11.89 μm.

Table 13 shows the influence of the applied process steps on the activity of Haemoctin®. The AUC values display the reduction of FVIII activity due to the different process conditions, pointing out the soft milling condition as the preferred one. This partial decrease of factor VIII activity will be equalized by dose adjustment, shown in Table 15.

Additionally Table 13 displays the behaviour of the activity in a kinetic period of 7 days, clearly indicating an improved half-life of FVIII activity at day 2 (77%) and day 7 (55%) for the 90/10 formulation (PLGA (LSB 5050 DLG 2A, d50=741 nm) (90%)/Haemoctin® (10%)="formulation 90") compressed with low pressure and milled under soft conditions. Still all the process steps have a positive influence on the activity left at day 7 compared to the Haemoctin® control.

TABLE 13

Activity kinetics of formulation 90 samples of different process steps.

| Formulation step [n = 3] with | Ratio Haemoctin® (%) | Ratio PLGA (%) | Lyophilisation | Tabletting single punch table press (low pressed) | Tabletting single punch table press (strong pressed) | Soft milling (1:-1) | Strong milling (1:-2) | Percentage of remaining | | | AUC against Haemoctin control (in vitro) 4 days |
|---|---|---|---|---|---|---|---|---|---|---|---|
| | | | | | | | | ~1h | 2d | 4d | |
| Haemoctin® | 100 | | | | | | | 100 | 70 | 23 | 100% |
| Formulation 90 | 10 | 90 | x | | | | | 100 | 63 | 55 | 76% |
| Formulation 90 | 10 | 90 | x | x | | | | 100 | 67 | 49 | 85% |
| Formulation 90 | 10 | 90 | x | | x | | | 100 | 66 | 59 | 94% |
| Formulation 90 | 10 | 90 | x | x | | | x | 100 | 55 | 42 | 25% |
| Formulation 90 | 10 | 90 | x | | x | | x | 100 | 68 | 53 | 25% |
| Formulation 90 | 10 | 90 | x | x | | x | | 100 | 77 | 55 | 51% |
| Formulation 90 | 10 | 90 | x | | x | x | | 100 | 66 | 58 | 51% |

In Table 14 it is shown that dry compression of FVIII with PLGA (LSB 5050 DLG 2A, d50=741 nm) even led to an improved FVIII activity of the recombinant factor VIII (Advate®) on day 2 of a kinetic compared to Advate® alone. The increase of activity above 100% for formulation 90/Haemoctin® on day 2 can be explained by the sustained release of Haemoctin® or rather FVIII out of the tablet.

TABLE 14

Activity kinetics of Haemoctin® or Advate® alone as well as their corresponding tablet prepared from a mixture of polymer with Haemoctin® or Advate®

| Formulation description | Ratio Advate® (%) | Ratio Haemoctin® (%) | Ratio PLGA (%) | Tabletting (handmade by Handi-Press) | Percentage of remaining | | |
|---|---|---|---|---|---|---|---|
| | | | | | ~1h | 2d | 7d |
| Haemoctin® (solution) | | 100 | | | 100 | 84 | 49 |
| Formulation 90/Haemoctin® | | 10 | 90 | x | 100 | 206 | 129 |
| Advate® (solution) | 100 | | | | 100 | 50 | 24 |
| Formulation 90/Advate® | 10 | | 90 | x | 100 | 65 | 22 |

As Table 13 pointed out the lyophilisation process together with low pressure tableting and soft milling conditions as the preferred formulation process, this process was further validated by additional process repetitions and activity kinetics.

This time the kinetics were performed with a dose-adjustment to 1 IU/mL as starting activity, taking into account the activity reduction caused by the process conditions applied; the results are shown in Table 15.

This dose-adjustment did not alter the effect of the formulation on the FVIII activity during the 7 day period.

TABLE 15

Activity kinetics of Haemoctin ® alone, lyophilised and the milled sample of a formulation 90 mixture including a sample with dose-adjustment.

| Formulation description [n = 3] with Haemoctin ® | Ratio Haemoctin ® (%) | Ratio PLGA (%) | Lyophili- sation | Tabletting eccentric press (low pressed) | Milling (1:-2) | Milling (1:-1) | Percentage of remaining ~1h | 2d | 7d | AUC against Haemoctin ® control (in vitro) 7 days | AUC against Haemoctin ® control (in vitro) 2 days |
|---|---|---|---|---|---|---|---|---|---|---|---|
| Haemoctin ® (solution) | 100 | | | | | | 100 | 70 | 23 | N/A | N/A |
| Formulation 90 | 10 | 90 | x | x | | x | 100 | 89 | 57 | N/A | N/A |
| Advate ® (1 IU adjusted) | 10 | 90 | x | x | | x | 100 | 88 | 60 | 81% | 153% |
| Haemoctin ® lyophilised (in vivo control) | 100 | | x | | | | 100 | 73 | 38 | 100% | 100% |

Again the formulation 90 samples displayed higher FVIII activities on day 2 and 7 of the kinetic.

The promising in vitro results for formulation 90 could also be confirmed by a 48 h in vivo study in mice displayed by the significantly increased area under the curve (AUC value) in table 15.

ATR-IR Spectroscopy

A small amount of dry sample was pressed on a carrier crystal (diamond) at a defined ohmic resistance (200Ω), followed by measurement of a full spectrum at 4000 to 400 $cm^{-1}$ using a Nicolet FT-IR spectrometer with additional ATR unit. Afterwards for interpretation of interactions between used substances and/or process steps, the specific band amide I (1700-1500 $cm^{-1}$) was considered in detail meaning six interval areas with a wavenumber range of 33.333 $cm^{-1}$ were fixed as analysis points. The resulting sample values display the percentage of each interval area to total measured amide I peak area.

TABLE 16

Interval areas of amide I band for factor VIII (FVIII, Haemoctin ®)/PLGA (LSB 5050 DLG 2A, d50 = 741 nm) formulation (*Subtraction result: Formulation - PLGA)

| Wavenumber area ($cm^{-1}$) | FVIII (%) | Form lyophiltzed* (%) | Form. tablet* (%) | Form. milled* (%) |
|---|---|---|---|---|
| 1700.000-1666.667 | 3.40 | 5.92 | 4.64 | 7.33 |
| 1667.667-1633.334 | 13.91 | 21.75 | 19.54 | 11.84 |
| 1633.334-1600.000 | 22.13 | 27.53 | 28.39 | 27.63 |
| 1600.000-1566.667 | 22.68 | 20.87 | 23.09 | 29.77 |
| 1566.667-1533.334 | 19.89 | 12.88 | 13.25 | 12.35 |
| 1533.334-1500.000 | 17.98 | 11.05 | 11.09 | 11.07 |

TABLE 17

Interval areas of amide I band for factor IX (FIX)/PLGA (LSB 5050 DLG 2A, d50 = 741 nm) formulation (*Subtraction result: Formulation - PLGA)

| Wavenumber area ($cm^{-1}$) | FIX (%) | Form. milled* (%) |
|---|---|---|
| 1700.000-1666.667 | 6.91 | 12.45 |
| 1667.667-1633.334 | 12.85 | 19.49 |

TABLE 17-continued

Interval areas of amide I band for factor IX (FIX)/PLGA (LSB 5050 DLG 2A, d50 = 741 nm) formulation (*Subtraction result: Formulation - PLGA)

| Wavenumber area ($cm^{-1}$) | FIX (%) | Form. milled* (%) |
|---|---|---|
| 1633.334-1600.000 | 19.44 | 24.61 |
| 1600.000-1566.667 | 25.19 | 22.71 |
| 1566.667-1533.334 | 21.90 | 13.05 |
| 1533.334-1500.000 | 13.71 | 7.68 |

TABLE 18

Interval areas of amide I band for von Willebrandt factor (vWF)/PLGA formulation (*Subtraction result: spectrum of the formulation subtracted by the spectrum of PLGA as background signal (almost zero) to evaluate the signals regarding the blood factor sample)

| Wavenumber area ($cm^{-1}$) | vWF (%) | Form. milled* (%) |
|---|---|---|
| 1700.000-1666.667 | 2.89 | 3.95 |
| 1667.667-1633.334 | 8.54 | 13.25 |
| 1633.334-1600.000 | 20.28 | 29.25 |
| 1600.000-1566.667 | 24.90 | 20.30 |
| 1566.667-1533.334 | 13.90 | 12.29 |
| 1533.334-1500.000 | 29.50 | 20.96 |

Table 16-18 show formulation (formulation 90%) dependent conformation/aggregation—changes of all three blood factors (FVIII, FIX and vWF). These changes result in a significant shift of the interval areas into the most sensitive part of the high energy region of amide I band around 1600 cm$^{-1}$ as well as larger contributions to this amide I area. In contrast PLGA (LSB 5050 DLG 2A, d50=741 nm) alone shows no signal in this area.

The invention claimed is:

1. A process for preparing a powder comprising at least one human coagulation factor protein and a lactic acid polymer, the process comprising the steps of:
   a) mixing and dispersing a lactic acid polymer with a particle size $d_{50}$ in the range 0.1-2 µm and at least one human coagulation factor protein in water to form a dispersion comprising the lactic acid polymer, the at least one human coagulation factor protein, and water,
   b) drying the dispersion to obtain a dried mass,
   c) compressing the dried mass from the dispersion to obtain a compressed dried mass, and
   d) comminuting the compressed dried mass from the dispersion to obtain the powder comprising the at least one human coagulation factor protein and the lactic acid polymer, wherein the powder has a particle size $d_{50}$ in the range of more than 0.5 and up to 5 µm.

2. The process according to claim 1, wherein the lactic acid polymer is a copolymer polymerized from a lactide unit and a glycolide unit.

3. The process according to claim 1, wherein the at least one human coagulation factor protein is at least one member selected from the group consisting of factor I=fibrinogen, factor II=prothrombin, factor III=tissue factor, factor V=proaccelerin, factor VII=proconvertin, factor VIII=antihemophilic factor A, factor IX=antihemophilic factor B, factor X=Stuart Prower factor, factor XI=plasma thromboplastin antecedent, factor XII=Hageman factor, factor XIII=fibrin-stabilizing factor, von Willebrand factor, prekallikrein, antithrombin III, heparin cofactor II, Protein C, Protein S, protein Z, protein Z-related proteinase inhibitor, plasminogen, alpha-plasma 2-antoplasmin, tissue plasminogen activator, urokinase, plasminogen activator inhibitor-1, and plasminogen activator inhibitor-2, and any combination thereof.

4. The process according to claim 1, wherein the human coagulation factor protein is comprised in a human blood plasma preparation.

5. The process according to claim 4, wherein the human coagulation factor protein is factor VIII, factor IX, von Willebrand factor or any combination thereof.

6. The process according to claim 4, wherein the human blood plasma preparation comprises von Willebrand factor in a not-physiological concentration.

7. The process according to claim 4, wherein the human blood plasma preparation comprises 0.05 to 5% by weight of human factor VIII and 95 to 99.95% by weight of at least one other plasma protein or a further pharmaceutical excipient or both.

8. The process according to claim 4, wherein the human blood plasma preparation comprises 25 to 1000 IU/ml of human factor VIII protein activity at a concentration of 100 mg/ml water.

9. The process according to claim 4, wherein, in step a), the ratio between the human blood plasma preparation, which comprises the human coagulation factor protein, and the lactic acid polymer, is from 30:70 to 5:95 parts by weight.

10. The process according claim 1, wherein the human coagulation factor protein is a recombinant factor VIII.

11. The process according to claim 1, wherein, in step a), a 5 to 50 fold excess of water by weight is used to nix and disperse the human factor VIII containing human blood plasma preparation and the lactic acid polymer.

12. The process according to claim 1, wherein, in step b), the drying of the dispersion is performed by lyophilization or by spray drying.

13. The process according to claim 1, wherein, in step c), the compression of dried mass from the dispersion is performed at a compression force from 0.2 to 2 kN.

14. A powder, obtainable by a process according to claim 1, wherein
   the powder comprises a human coagulation factor protein and a lactic acid polymer, and
   the powder has a particle size $d_{50}$ in the range of 0.5 to 5 µm.

15. A pharmaceutical composition, comprising:
   the powder according to claim 14 in dry, dispersed, or dissolved form.

16. A method for producing a pharmaceutical composition, the method comprising:
   adding the powder according to claim 14 to the pharmaceutical composition.

17. The method according to claim 16, wherein said pharmaceutical composition is suitable for the treatment of a disease or a genetic disorder associated with the human coagulation factor protein.

* * * * *